United States Patent
Mayer

(10) Patent No.: US 9,364,339 B2
(45) Date of Patent: Jun. 14, 2016

(54) UNILATERALLY PLACED EXPANSILE SPINAL PROSTHESIS

(71) Applicant: Peter L. Mayer, Sarasota, FL (US)

(72) Inventor: Peter L. Mayer, Sarasota, FL (US)

( * ) Notice: Subject to any disclaimer, the term of this patent is extended or adjusted under 35 U.S.C. 154(b) by 270 days.

(21) Appl. No.: 13/845,877

(22) Filed: Mar. 18, 2013

(65) Prior Publication Data

US 2013/0317617 A1 Nov. 28, 2013

Related U.S. Application Data

(60) Provisional application No. 61/640,230, filed on Apr. 30, 2012.

(51) Int. Cl.
 *A61F 2/44* (2006.01)
 *A61F 2/46* (2006.01)
 *A61F 2/30* (2006.01)

(52) U.S. Cl.
 CPC .............. *A61F 2/442* (2013.01); *A61F 2/4611* (2013.01); *A61F 2002/30235* (2013.01);
 (Continued)

(58) Field of Classification Search
 CPC .. A61B 17/88; A61B 17/844; A61B 17/7258; A61B 17/7225; A61B 17/8858; A61B 17/66; A61B 17/7275; A61B 2017/042; A61F 2/4611; A61F 2/442; A61F 2/44; A61F 2002/30484; A61F 2002/4435; A61F 2002/4627
 USPC ................... 606/105, 310, 313, 326, 327, 68; 623/17.11–17.16
 See application file for complete search history.

(56) References Cited

U.S. PATENT DOCUMENTS 725,874 A * 4/1903 Riley .......................... 269/48.1
 2,485,531 A 10/1949 Dzus
 (Continued)

FOREIGN PATENT DOCUMENTS

DE 4208116 9/1993
DE WO 2011/048140 A1 * 4/2011 ............. A61B 17/88
 (Continued)

OTHER PUBLICATIONS

International Preliminary Report on Patentability and Written Opinion dated Mar. 22, 2011 for PCT/US2009/057369 filed Sep. 17 2009.
(Continued)

*Primary Examiner* — Eduardo C Robert
*Assistant Examiner* — Michelle C Eckman
(74) *Attorney, Agent, or Firm* — Fleit Gibbons Gutman Bongini & Bianco PL

(57) ABSTRACT

An expandable spinal prosthesis is provided for insertion unilaterally into an annulotomy hole created laterally in a spinal disc between two abutting vertebrae. The prosthesis is composed of an elongated rod having first threading at one end and second threading at its other end. A first member is threaded on the threading at one end of the rod. A second member is threaded on the threading at the other end of the rod. The members are disengageably engaged for rotation together. The first member has a plurality of resilient bands extending longitudinally between the two members, which are dependent on the spacing between the two members. The first member and the elongated rod define engagements for coupling of drivers to relatively rotate the members and rod in one sense so that the two members will move toward each other to cause the resilient bands to bend outwardly to expand the prosthesis and in an opposite sense so that the two members will move apart to cause the resilient bands to become unbent and collapse the prosthesis. A method for implanting the prosthesis from one side only and a method for explanting the prosthesis from one side only.

10 Claims, 18 Drawing Sheets

(52) U.S. Cl.
CPC .......... *A61F 2002/30286* (2013.01); *A61F 2002/30411* (2013.01); *A61F 2002/30507* (2013.01); *A61F 2002/30579* (2013.01); *A61F 2002/30594* (2013.01); *A61F 2002/444* (2013.01); *A61F 2002/4629* (2013.01)

(56) References Cited

U.S. PATENT DOCUMENTS

| | | | |
|---|---|---|---|
| 3,986,383 A * | 10/1976 | Petteys ........................... 72/393 |
| 4,041,939 A | 8/1977 | Hall |
| 4,349,921 A | 9/1982 | Kuntz |
| 4,465,220 A * | 8/1984 | Ledlow et al. .................. 228/50 |
| 4,772,287 A | 9/1988 | Ray et al. |
| 4,863,476 A * | 9/1989 | Shepperd .................... 623/17.15 |
| 4,865,604 A * | 9/1989 | Rogozinski ................ 623/23.42 |
| 4,944,753 A | 7/1990 | Burgess |
| 4,973,301 A * | 11/1990 | Nissenkorn ...................... 604/8 |
| 5,047,055 A | 9/1991 | Bao et al. |
| 5,059,193 A * | 10/1991 | Kuslich ......................... 606/247 |
| 5,100,405 A | 3/1992 | McLaren |
| 5,171,278 A * | 12/1992 | Pisharodi ...................... 128/898 |
| 5,298,254 A | 3/1994 | Prewett |
| 5,390,683 A * | 2/1995 | Pisharodi ................ A61F 2/442 128/898 |
| 5,454,365 A * | 10/1995 | Bonutti ......................... 600/204 |
| 5,456,667 A * | 10/1995 | Ham et al. ..................... 604/107 |
| 5,514,180 A | 5/1996 | Heggeness |
| 5,545,229 A | 8/1996 | Parsons et al. |
| 5,562,735 A | 10/1996 | Margulies |
| 5,571,189 A | 11/1996 | Kuslich |
| 5,653,763 A * | 8/1997 | Errico et al. ............... 623/17.11 |
| 5,662,657 A | 9/1997 | Carn |
| 5,693,100 A * | 12/1997 | Pisharodi ................... 623/17.16 |
| 5,865,846 A | 2/1999 | Bryan |
| 5,919,194 A * | 7/1999 | Anderson ..................... 606/313 |
| 5,951,553 A | 9/1999 | Betz |
| 5,964,807 A | 10/1999 | Gan |
| 6,048,342 A | 4/2000 | Zucherman |
| 6,063,121 A | 5/2000 | Xavier et al. |
| 6,093,205 A | 7/2000 | McLeod et al. |
| 6,110,210 A | 8/2000 | Norton et al. |
| 6,126,688 A | 10/2000 | McDonnell |
| 6,146,420 A | 11/2000 | McKay |
| 6,146,422 A | 11/2000 | Lawson |
| 6,214,012 B1 | 4/2001 | Karpman |
| 6,224,600 B1 * | 5/2001 | Protogirou ..................... 606/63 |
| 6,240,926 B1 | 6/2001 | Chin Gan |
| 6,264,695 B1 | 7/2001 | Stoy |
| 6,287,308 B1 | 9/2001 | Betz |
| 6,319,255 B1 * | 11/2001 | Grundei et al. .................. 606/76 |
| 6,368,319 B1 | 4/2002 | Schaefer |
| 6,395,034 B1 | 5/2002 | Suddaby |
| 6,419,704 B1 | 7/2002 | Ferree |
| 6,419,706 B1 | 7/2002 | Graf |
| 6,451,020 B1 | 9/2002 | Zucherman et al. |
| 6,451,057 B1 * | 9/2002 | Chen et al. .................. 623/17.15 |
| 6,494,883 B1 * | 12/2002 | Ferree .......................... 606/247 |
| 6,500,178 B2 | 12/2002 | Zucherman et al. |
| 6,500,182 B2 * | 12/2002 | Foster ........................... 606/127 |
| 6,500,206 B1 | 12/2002 | Bryan |
| 6,554,833 B2 * | 4/2003 | Levy et al. ...................... 606/63 |
| 6,582,467 B1 * | 6/2003 | Teitelbaum et al. ......... 623/17.11 |
| 6,632,224 B2 | 10/2003 | Cachia |
| 6,676,665 B2 * | 1/2004 | Foley et al. .................... 606/105 |
| 6,733,531 B1 | 5/2004 | Trieu |
| 6,780,175 B1 * | 8/2004 | Sachdeva et al. .............. 604/531 |
| 6,821,298 B1 * | 11/2004 | Jackson .................... 623/17.15 |
| 6,929,640 B1 | 8/2005 | Underwood |
| 6,966,930 B2 * | 11/2005 | Arnin et al. ................ 623/17.11 |
| 6,974,479 B2 | 12/2005 | Trieu |
| 6,997,929 B2 | 2/2006 | Manzi |
| 7,001,431 B2 | 2/2006 | Bao et al. |
| 7,004,971 B2 | 2/2006 | Serhan et al. |
| 7,048,764 B2 | 5/2006 | Ferree |
| 7,101,400 B2 | 9/2006 | Thramann |
| 7,153,305 B2 | 12/2006 | Johnson |
| 7,204,853 B2 | 4/2007 | Gordon |
| 7,238,206 B2 | 7/2007 | Lange |
| 7,250,060 B2 | 7/2007 | Trieu |
| 7,261,738 B2 | 8/2007 | Casey |
| 7,270,682 B2 | 9/2007 | Frigg et al. |
| 7,371,238 B2 | 5/2008 | Soboleski |
| 7,452,369 B2 | 11/2008 | Barry |
| 7,491,236 B2 | 2/2009 | Cragg |
| 7,569,055 B2 | 8/2009 | Zander |
| 7,601,152 B2 * | 10/2009 | Levy et al. ...................... 606/63 |
| 7,621,950 B1 * | 11/2009 | Globerman et al. ........ 623/17.11 |
| 7,758,644 B2 * | 7/2010 | Trieu .......................... 623/17.11 |
| 7,763,074 B2 * | 7/2010 | Altarac et al. ............. 623/17.11 |
| 7,799,056 B2 * | 9/2010 | Sankaran ..................... 606/246 |
| 7,799,081 B2 * | 9/2010 | McKinley .................. 623/17.16 |
| 7,824,429 B2 | 11/2010 | Culbert |
| 7,959,652 B2 * | 6/2011 | Zucherman et al. .......... 606/249 |
| 8,092,459 B2 * | 1/2012 | Malandain ................ 606/86 A |
| 8,096,994 B2 * | 1/2012 | Phan et al. ................. 606/86 A |
| 8,097,018 B2 * | 1/2012 | Malandain et al. ........... 606/246 |
| 8,100,943 B2 * | 1/2012 | Malandain et al. ........... 606/246 |
| 8,105,358 B2 * | 1/2012 | Phan ............................ 606/249 |
| 8,187,333 B2 | 5/2012 | Mayer |
| 8,241,335 B2 * | 8/2012 | Truckai et al. ............... 606/279 |
| 8,262,736 B2 | 9/2012 | Michelson |
| 8,323,344 B2 * | 12/2012 | Galley et al. ............... 623/17.16 |
| 8,409,282 B2 * | 4/2013 | Kim ........................... 623/17.11 |
| 8,512,407 B2 * | 8/2013 | Butler et al. ............... 623/17.16 |
| 8,518,115 B2 * | 8/2013 | Chavatte et al. ............ 623/17.12 |
| 8,529,628 B2 * | 9/2013 | Marino et al. .............. 623/17.16 |
| 8,556,949 B2 * | 10/2013 | Teisen et al. ................. 606/327 |
| 8,641,769 B2 * | 2/2014 | Malandain ................. 623/17.16 |
| 8,784,491 B2 * | 7/2014 | Biedermann et al. ....... 623/17.11 |
| 8,814,908 B2 * | 8/2014 | Druma et al. ................. 606/248 |
| 8,821,497 B2 | 9/2014 | Stupak |
| 8,906,022 B2 * | 12/2014 | Krinke et al. ................... 606/63 |
| 8,940,048 B2 * | 1/2015 | Butler et al. ............... 623/17.15 |
| 8,961,518 B2 * | 2/2015 | Taylor et al. .................... 606/79 |
| 8,986,386 B2 * | 3/2015 | Oglaza et al. .............. 623/17.15 |
| 9,039,742 B2 * | 5/2015 | Altarac et al. ................ 606/249 |
| 2002/0022887 A1 * | 2/2002 | Huene ........................ 623/17.16 |
| 2002/0120334 A1 | 8/2002 | Crozet |
| 2002/0183848 A1 | 12/2002 | Ray et al. |
| 2003/0176921 A1 | 9/2003 | Lawson |
| 2003/0181979 A1 * | 9/2003 | Ferree ........................ 623/17.11 |
| 2003/0204260 A1 | 10/2003 | Ferree |
| 2004/0010317 A1 | 1/2004 | Lambrechi et al. |
| 2004/0097927 A1 * | 5/2004 | Yeung et al. .................... 606/61 |
| 2004/0133204 A1 * | 7/2004 | Davies ........................... 606/63 |
| 2004/0204763 A1 * | 10/2004 | Ralph et al. ................ 623/17.13 |
| 2004/0258732 A1 | 12/2004 | Shikinami |
| 2004/0260297 A1 | 12/2004 | Padget |
| 2005/0015150 A1 | 1/2005 | Lee |
| 2005/0015152 A1 | 1/2005 | Sweeney |
| 2005/0113919 A1 | 5/2005 | Cragg et al. |
| 2005/0113923 A1 | 5/2005 | Acker et al. |
| 2005/0113929 A1 | 5/2005 | Cragg |
| 2005/0143827 A1 * | 6/2005 | Globerman et al. ........ 623/17.16 |
| 2005/0182414 A1 | 8/2005 | Manzi |
| 2005/0187559 A1 | 8/2005 | Raymond |
| 2005/0222681 A1 * | 10/2005 | Richley et al. ............. 623/17.11 |
| 2005/0234557 A1 * | 10/2005 | Lambrecht ........... A61B 5/1076 623/17.16 |
| 2005/0261781 A1 * | 11/2005 | Sennett et al. .............. 623/23.54 |
| 2005/0273166 A1 * | 12/2005 | Sweeney .................... 623/17.11 |
| 2005/0278028 A1 * | 12/2005 | Mujwid ...................... 623/17.13 |
| 2005/0278036 A1 * | 12/2005 | Leonard et al. ............. 623/23.47 |
| 2006/0136061 A1 | 6/2006 | Navarro et al. |
| 2006/0161166 A1 | 7/2006 | Johnson |
| 2006/0235417 A1 * | 10/2006 | Sala ............................... 606/79 |
| 2006/0235534 A1 | 10/2006 | Gertzman et al. |
| 2006/0253132 A1 | 11/2006 | Evans |
| 2006/0253198 A1 | 11/2006 | Myint et al. |
| 2006/0271061 A1 * | 11/2006 | Beyar et al. ................... 606/105 |
| 2006/0276790 A1 * | 12/2006 | Dawson et al. ................. 606/61 |
| 2006/0276897 A1 | 12/2006 | Winslow et al. |
| 2006/0276901 A1 | 12/2006 | Zipnick et al. |
| 2006/0276902 A1 | 12/2006 | Zipnick et al. |

(56) References Cited

U.S. PATENT DOCUMENTS

| | | |
|---|---|---|
| 2006/0287730 A1 | 12/2006 | Segal et al. |
| 2007/0010889 A1 | 1/2007 | Francis |
| 2007/0027546 A1 | 2/2007 | Palm et al. |
| 2007/0038222 A1 | 2/2007 | Bhatnagar et al. |
| 2007/0038301 A1 | 2/2007 | Hudgins |
| 2007/0043440 A1* | 2/2007 | William et al. ............ 623/17.11 |
| 2007/0050037 A1 | 3/2007 | Snell et al. |
| 2007/0061012 A1 | 3/2007 | Cauthen, III |
| 2007/0067034 A1* | 3/2007 | Chirico et al. ............. 623/17.11 |
| 2007/0067039 A1 | 3/2007 | Lambrecbt et al. |
| 2007/0073402 A1 | 3/2007 | Vresilovic et al. |
| 2007/0088436 A1* | 4/2007 | Parsons et al. ............. 623/17.11 |
| 2007/0173826 A1* | 7/2007 | Canaveral et al. ............. 606/61 |
| 2007/0173939 A1* | 7/2007 | Kim et al. .................. 623/17.11 |
| 2007/0179612 A1 | 8/2007 | Johnson |
| 2007/0219634 A1* | 9/2007 | Greenhalgh et al. ....... 623/17.16 |
| 2007/0239280 A1 | 10/2007 | Keith |
| 2008/0009875 A1* | 1/2008 | Sankaran et al. ................ 606/84 |
| 2008/0039944 A1* | 2/2008 | Malandain et al. ........ 623/17.16 |
| 2008/0051893 A1* | 2/2008 | Malandain et al. ........ 623/17.11 |
| 2008/0051894 A1* | 2/2008 | Malandain et al. ........ 623/17.11 |
| 2008/0051895 A1* | 2/2008 | Malandain et al. ........ 623/17.11 |
| 2008/0058934 A1* | 3/2008 | Malandain et al. ........ 623/17.11 |
| 2008/0071356 A1* | 3/2008 | Greenhalgh et al. .......... 623/1.16 |
| 2008/0183204 A1* | 7/2008 | Greenhalgh et al. .......... 606/198 |
| 2008/0221624 A1* | 9/2008 | Gooch ......................... 606/302 |
| 2008/0262617 A1* | 10/2008 | Froehlich et al. ........... 623/14.12 |
| 2008/0281346 A1* | 11/2008 | Greenhalgh et al. .......... 606/191 |
| 2008/0281364 A1* | 11/2008 | Chirico et al. ............. 606/86 A |
| 2009/0005821 A1* | 1/2009 | Chirico et al. ................ 606/319 |
| 2009/0012564 A1* | 1/2009 | Chirico et al. ................ 606/246 |
| 2009/0024157 A1* | 1/2009 | Anukhin ....................... 606/200 |
| 2009/0054935 A1* | 2/2009 | Miller et al. ................. 606/86 R |
| 2009/0204216 A1* | 8/2009 | Biedermann et al. ...... 623/17.12 |
| 2009/0292323 A1* | 11/2009 | Chirico et al. ............. 606/86 R |
| 2010/0070035 A1* | 3/2010 | Mayer ................... A61F 2/442 623/17.16 |
| 2010/0185287 A1* | 7/2010 | Allard et al. ................ 623/17.11 |
| 2010/0185291 A1* | 7/2010 | Jimenez et al. ............. 623/17.16 |
| 2010/0217325 A1* | 8/2010 | Hochschuler et al. ........ 606/264 |
| 2010/0228301 A1* | 9/2010 | Greenhalgh et al. .......... 606/313 |
| 2011/0029082 A1* | 2/2011 | Hall ........................... 623/17.11 |
| 2011/0230965 A1 | 9/2011 | Schell |
| 2011/0270396 A1* | 11/2011 | Leibowitz .................. 623/17.11 |
| 2012/0004732 A1* | 1/2012 | Goel et al. .................. 623/17.16 |
| 2012/0046748 A1* | 2/2012 | Weiman ..................... 623/17.16 |
| 2012/0265304 A1* | 10/2012 | Mayer ........................ 623/17.12 |
| 2013/0158669 A1* | 6/2013 | Sungarian et al. .......... 623/17.16 |
| 2013/0190877 A1* | 7/2013 | Medina ...................... 623/17.16 |
| 2013/0197642 A1* | 8/2013 | Ernst .......................... 623/17.16 |
| 2013/0197647 A1* | 8/2013 | Wolters et al. ............. 623/17.16 |
| 2013/0226251 A1* | 8/2013 | Chegini et al. ................ 606/325 |
| 2013/0310883 A1* | 11/2013 | Levy et al. .................... 606/313 |
| 2013/0310936 A1* | 11/2013 | Mayer ........................ 623/17.15 |
| 2013/0317617 A1* | 11/2013 | Mayer ........................ 623/17.16 |
| 2014/0012336 A1* | 1/2014 | Biedermann et al. .......... 606/313 |
| 2014/0031940 A1* | 1/2014 | Banouskou ................. 623/17.16 |
| 2014/0121775 A1* | 5/2014 | Hardenbrook et al. .... 623/17.16 |
| 2014/0243982 A1* | 8/2014 | Miller ........................ 623/17.16 |
| 2014/0257484 A1* | 9/2014 | Flower et al. .............. 623/17.15 |
| 2014/0350608 A1* | 11/2014 | Goel et al. ..................... 606/279 |
| 2015/0012098 A1* | 1/2015 | Eastlack et al. ............ 623/17.15 |

FOREIGN PATENT DOCUMENTS

| | | |
|---|---|---|
| EP | 0042271 | 12/1981 |
| FR | 2639823 | 6/1990 |
| FR | 2723841 | 3/1996 |
| FR | 2772594 | 6/1999 |
| FR | 2862866 | 6/2005 |
| WO | 0013620 | 3/2000 |
| WO | 0013691 | 3/2000 |
| WO | 2004064692 | 8/2004 |
| WO | 2004089240 | 10/2004 |
| WO | 2005084589 | 9/2005 |
| WO | 2006078663 | 7/2006 |
| WO | 2007048252 | 5/2007 |

OTHER PUBLICATIONS

International Search Report dated May 4, 2010 for PCT/US2009/057369 filed Sep. 17, 2009.

* cited by examiner

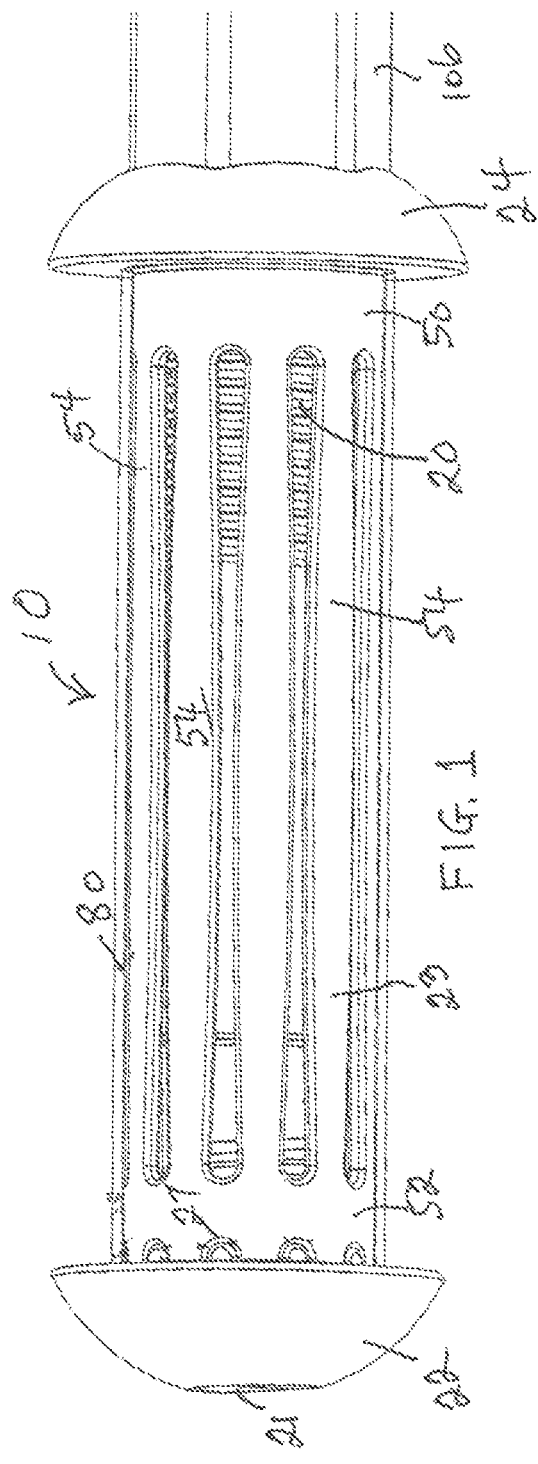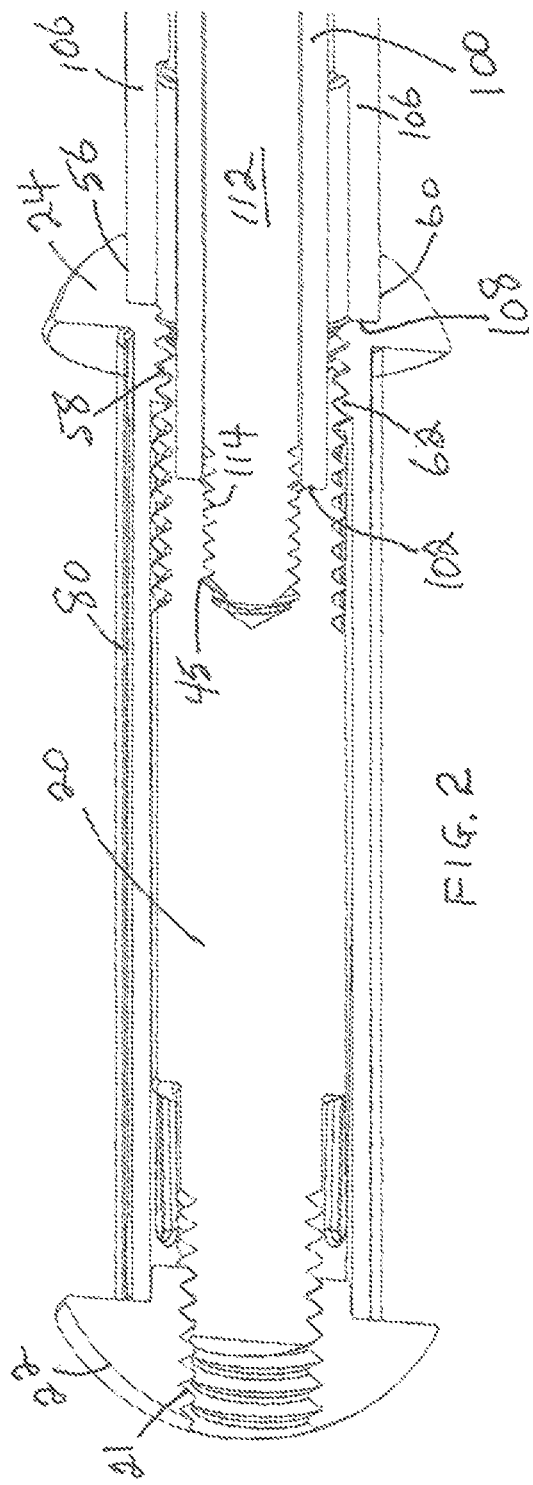

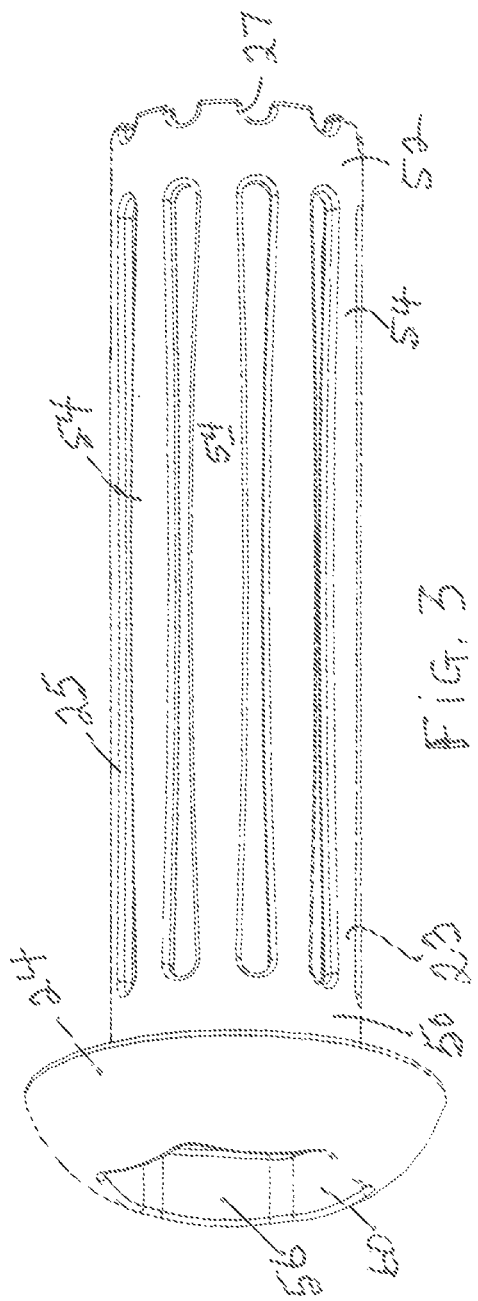
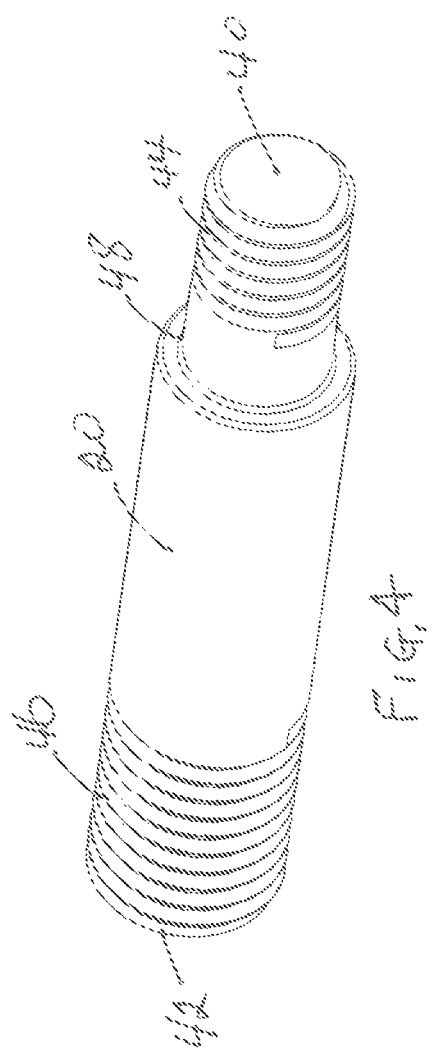

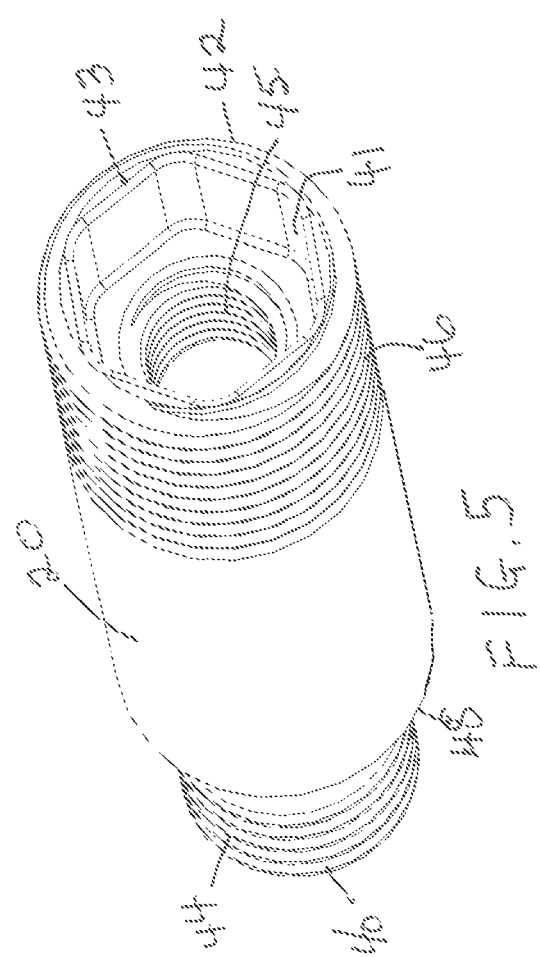

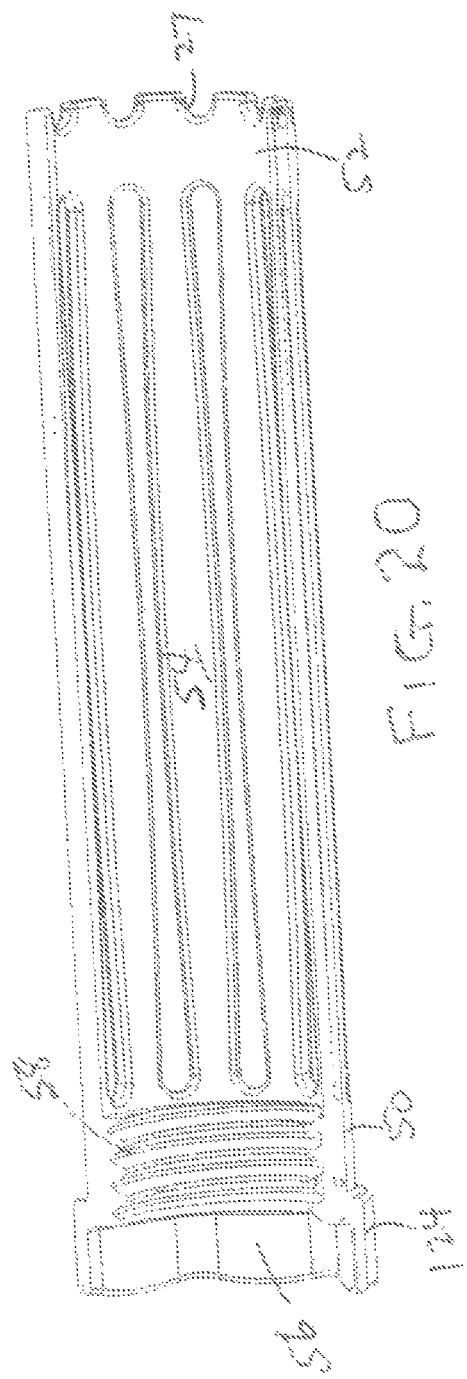

UNILATERALLY PLACED EXPANSILE SPINAL PROSTHESIS

CROSS REFERENCE TO RELATED APPLICATION

This application is related to and claims priority from U.S. Provisional Application No. 61/640,230 filed on Apr. 30, 2012, herein incorporated by reference in its entirety.

BACKGROUND

Intervertebral discs (or more simply "discs") lie between adjacent vertebrae in the spine. Each disc forms a cartilaginous joint to allow slight movement of the vertebrae and acts as a ligament to hold the vertebrae together.

Discs include an outer annulus fibrosus, which surrounds the inner nucleus pulposus. The annulus fibrosus includes several layers of fibrocartilage. The nucleus pulposus contains loose fibers suspended in a mucoprotein gel, which has the consistency of semi-hard and slightly fibrous connective tissue or cartilage. The nucleus of the disc acts as a shock absorber for distributing pressure evenly across the disc and for absorbing the impact of bending and twisting of the spine while keeping the two abutting vertebrae separated. When one develops a prolapsed disc, the nucleus pulposus is forced out resulting in pressure being put on nerves located near the disc. This can cause severe pain and neurological problems.

There is one disc between each pair of adjacent vertebrae, except between the first and second cervical vertebrae. The atlas is the first cervical (neck) vertebra which is just under the head. The axis is the second cervical vertebra. The axis acts as a post around which the atlas can rotate, allowing the neck to rotate. There are a total of twenty-three discs in the spine. The discs are most commonly identified by specifying the particular vertebrae they separate. For example, the disc between the fifth and sixth cervical vertebrae is designated "C5-6".

As people age, intervertebral discs tend to degenerate. Two typical processes can occur. The nucleus pulposus dehydrates and flattens, which limits its ability to absorb shock. The annulus fibrosus gets weaker with age and develops fissures or tears. As the discs dehydrate, the disc spaces change and the space for adjacent nerves narrows. In the neural foramens, this is called foraminal stenosis; in the spinal canal, this is called central stenosis. The discs bulge outward, and bone spurs (osteophytes) form along the bulging disc surfaces that also pinch adjacent nerves (spinal cord, cauda equina, and nerve roots). A flattening disc causes stress to the posterior elements of the spine and also the facet joints. Although these conditions may not cause pain in some people, others experience acute and chronic pain.

Pain, weakness, and numbness due to pinching of the nerves protruding from the spine are called radiculopathy or radiculitis. Pain, weakness, and numbness due to pinching of the nerves inside the spinal canal is known as radiculopathy, radiculitis, cauda equina syndrome or myelopathy, depending on the level of the spine and the type of symptoms.

When the annulus fibrosus tears due to an injury or the degenerative process, the nucleus pulposus may begin to extrude through the tear. This is called disc herniation. Near the posterior aspect of each disc, at each vertebral level or segment, a pair of major spinal nerves extends outward, to different organs, tissues, extremities, etc. Herniated discs often press against these nerves (pinched nerve) and the spinal cord causing neurologic dysfunction including sensory and/or motor loss and/or pain.

Herniated disc, ruptured disc, bulging disc, degenerative disc, protrusion, extrusion, all refer to related processes and are used more-or-less synonymously, depending on the medical professional. There is no true standard nomenclature, and the various terms mean different things to different people. Also, the degree to which there is pressure on the nerves (e.g. stenosis, pinching, nerve root elevation, cord compression, effacement, and many other descriptions) also varies.

To treat impaired discs, many techniques and devices have been used. Some treatments remove, dissolve, or vaporize disc material (e.g. chymopapain injection, microsurgical discectomy, nucleotomy, laser discectomy, radiofrequency ablation, and others). Other treatments fuse the disc (e.g. cages, screws, bone grafts, bone morphogenic protein, and others). Disc removal procedures remove the disc. Fusion procedures result in loss of motion of the disc and juxtaposed vertebrae.

Accordingly, there is a need for an implantable prosthesis that treats the conditions noted above in a more efficacious manner to restore to a damaged disc area the original natural body motion function.

SUMMARY OF THE INVENTION

This existing need is met by the implantable prosthesis of the present invention, which is easily and quickly implantable. The implantable prosthesis is inserted into a damaged intervertebral disc. Structurally, the prosthesis has an elongated tubular main prosthesis body with a length to fit laterally from one side of a disc to the other at its mid-plane. The main prosthesis body either has a vertical height slightly greater than the height of normal disc space of the damaged intervertebral disc into which it is to be implanted, or is expandable to a vertical height slightly greater than the height of normal disc space of the damaged intervertebral disc into which it is to be implanted. The prosthesis has a shape in cross section normal to its longitudinal axis so that main prosthesis body makes appropriate contact with vertebrae abutting to the damaged intervertebral disc. In the first embodiment, heads positioned on the ends of the main prosthesis body may have a vertical height greater than the vertical height of the main prosthesis body. The invention also includes a method for implanting from one side only and a method for explanting from one side only. Other embodiments include a prosthesis with only a head on one end (the proximal end) of the main prosthesis body that is a greater vertical height than that of the main prosthesis body and a prosthesis with both heads substantially equal in vertical height to the main body of the prosthesis, i.e. a prosthesis that is to be implanted entirely within the intervertebral disc.

BRIEF DESCRIPTION OF THE DRAWINGS

FIG. 1 is a side view of an expansible prosthesis with implanting tools coupled;

FIG. 2 is a sectional view taken through the mid-plane of the prosthesis of FIG. 1;

FIG. 3 is a perspective view of the main body portion of the prosthesis;

FIG. 4 is a perspective view of the rod serving as a lead screw of the prosthesis;

FIG. 5 is another perspective view of the rod shown in FIG. 4;

FIG. 20 is a sectional view through the mid-plane of the main body shown in FIG. 19.

DETAILED DESCRIPTION OF PREFERRED EMBODIMENTS OF THE INVENTION

Figure 14:
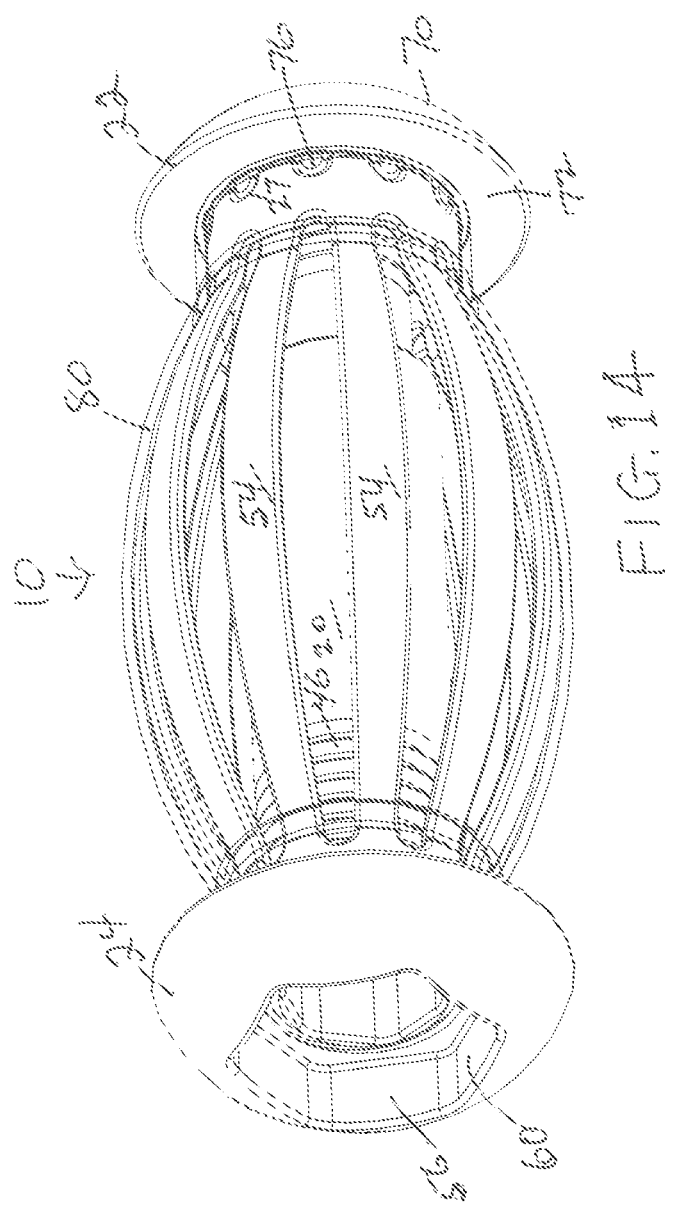
FIG. 14 is a perspective view of the prosthesis expanded.
Figure 15:
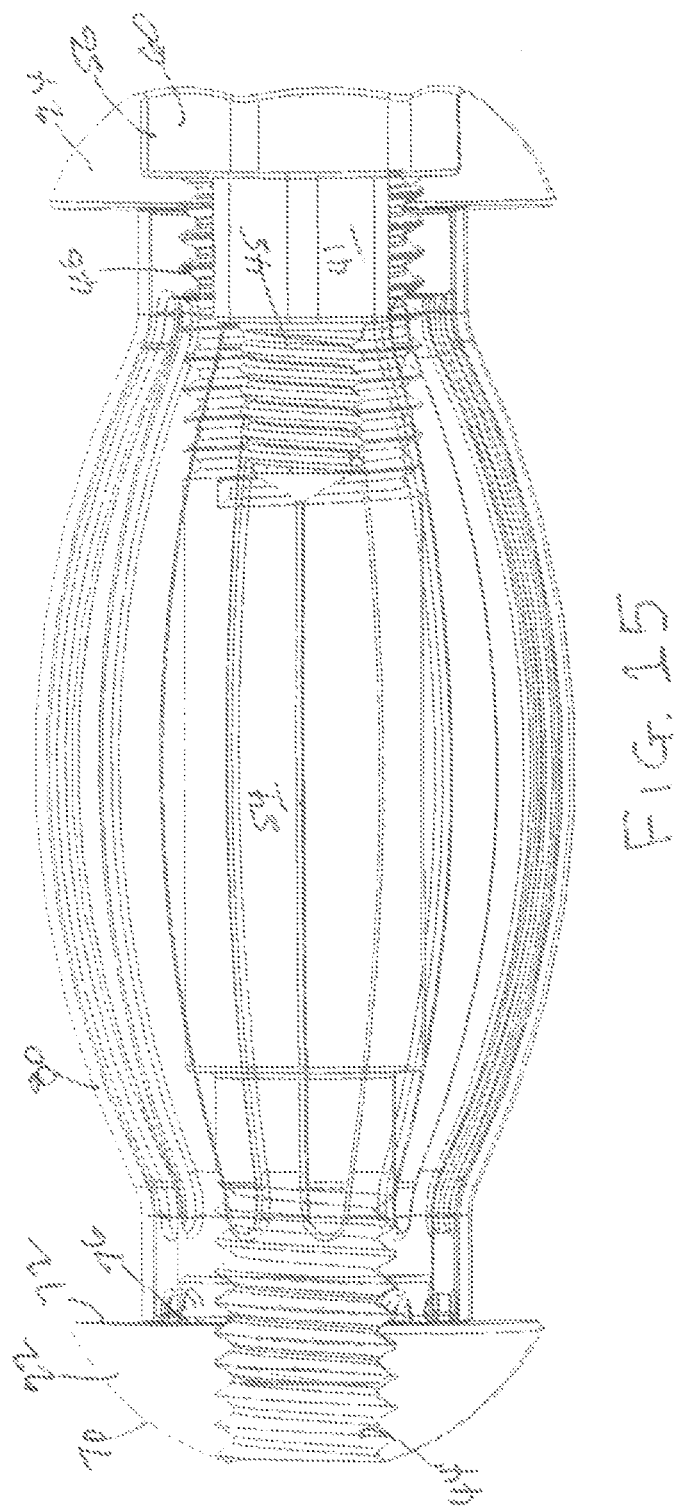
FIG. 15 is a sectional view through the mid-plane of the expanded prosthesis.

An expandable spinal prosthesis 10 for insertion into an annulotomy hole created laterally in a spinal disc between two abutting vertebrae is shown in FIGS. 1-8. As shown, the novel spinal prosthesis device 10 is in repose or at rest condition. FIGS. 14 and 15 show the novel spinal prosthesis device 10 expanded to distract intentionally the abutting vertebrae. The prosthesis is somewhat longer than the lateral width of the spinal disc so that when implanted, it will expand and the length will be shortened to abut the adjacent vertebrae.

The prosthesis consists of four components, namely, a main body 23 with a proximal cap 24, a distal end cap 22, a rod or lead screw 20, and a membrane 80. The rod or lead screw 20 consists of a shaft that has a proximal end 42 of larger diameter than its distal end 40. A shoulder 48 is defined between the two ends. The larger end 42 has a threading 46 and the smaller diameter end 40 has a threading 44. The larger end 42 is recessed 43 to define a proximally larger portion 41 that has a hex shape and a distally narrower portion that contains threading 45. The main body portion 23 consists of a flanged proximal end cap 24 fixed or integrated with a hollow tube 25. Tube 25 consists of a proximal ring 50 and distal ring 52 interconnected about their peripheries by longitudinally extending, peripherally spaced bands 54. Proximal end cap 24 is recessed to define a proximal portion 56 that is hex shaped 60, and a distal portion that is threaded 58 to match the threads 46 of rod 20. The tube 25 is made of a material, such as, Stainless Steel that is resilient and can be bent and deformed outwardly without exceeding its elastic limit. The distal end, ring 52, of tube 25 is open and its end face defines a plurality of peripherally spaced cutouts 27. The distal flanged end cap 22 consists of a convex outer surface 70, a flat inside surface 72, and a projecting annular ring 73. Projections 76 extend radially from the annular surface 74 of the annular ring 73 in radial alignment with the cutouts 27 of the tube 25. A hole 21 is defined axially through the cap 22 and its surface is threaded 78 to match the threads 44 of rod 20. A transparent resilient membrane 80 surrounds the tube 25 and extends longitudinally from proximal end cap 24 to distal end cap 22.

Figure 11:
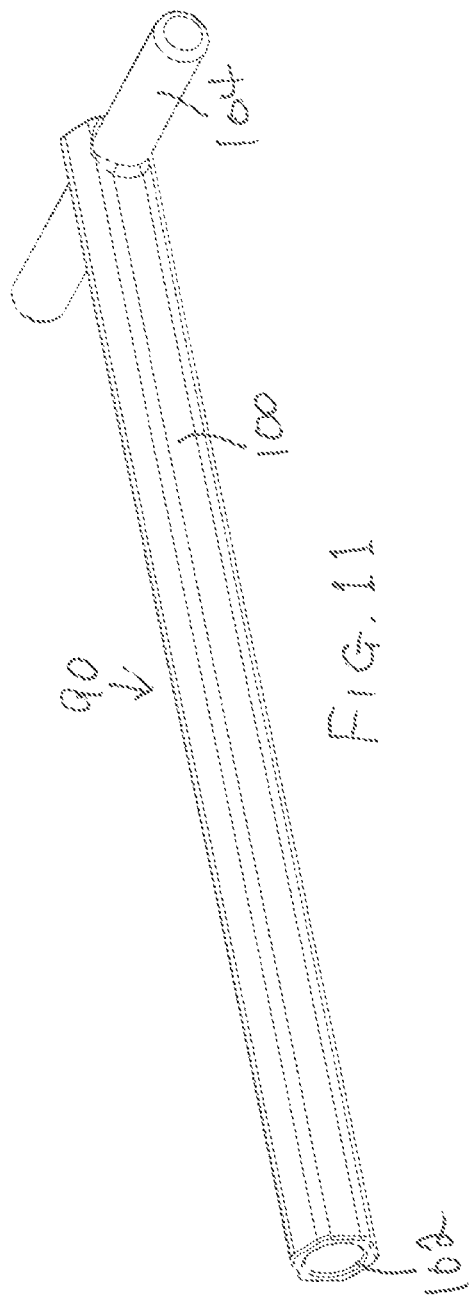
FIG. 11 is a hex tool for implanting the prosthesis.
Figure 12:
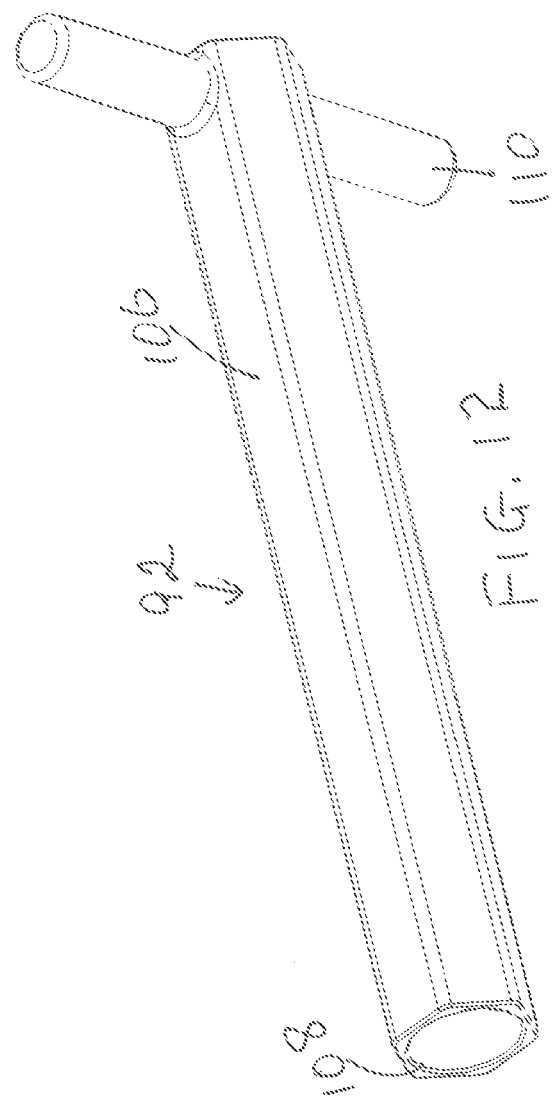
FIG. 12 is another hex tool for implanting the prosthesis.
Figure 13:
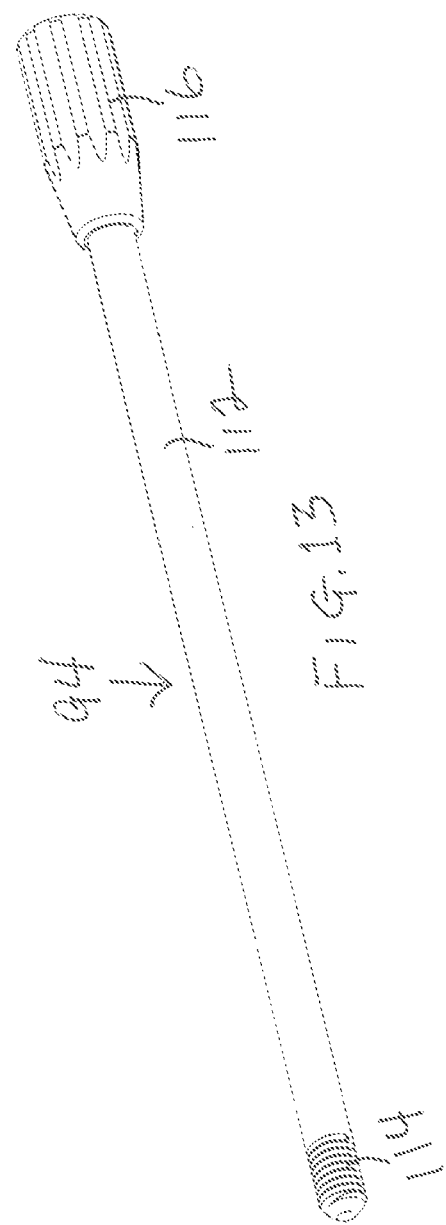
FIG. 13 is a lead screw tool for coupling with the prosthesis.

Implant tools are shown in FIGS. 11 to 13. A first hex tool 90 is shown in FIG. 11 and consists of a hollow hex tube 100 having a distal hex opening 102 and a proximal handle 104 that does not obstruct the hex tube proximal end opening. A second hex tool 92 is shown in FIG. 12 and consists of a hollow hex tube 106 having a distal hex opening 108 and a proximal handle 110 that does not obstruct the hex tube proximal end opening. A lead screw tool 94 is shown in FIG. 13 and consists of a rod 112 having threading 114 on its proximal end and a knurled knob 116 on its proximal end.

Figure 6:
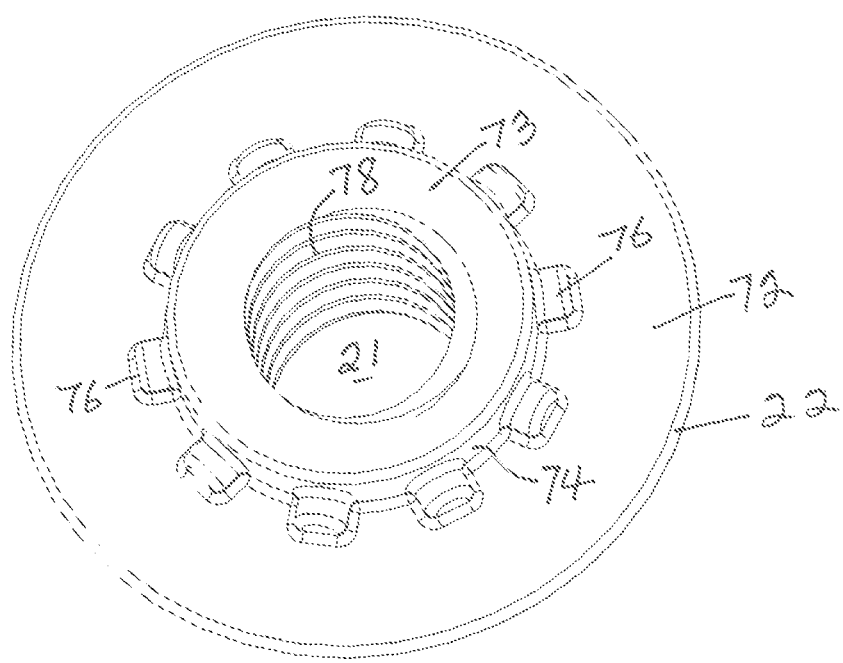
FIG. 6 is a perspective view of the distal end cap of the prosthesis.
Figure 7:
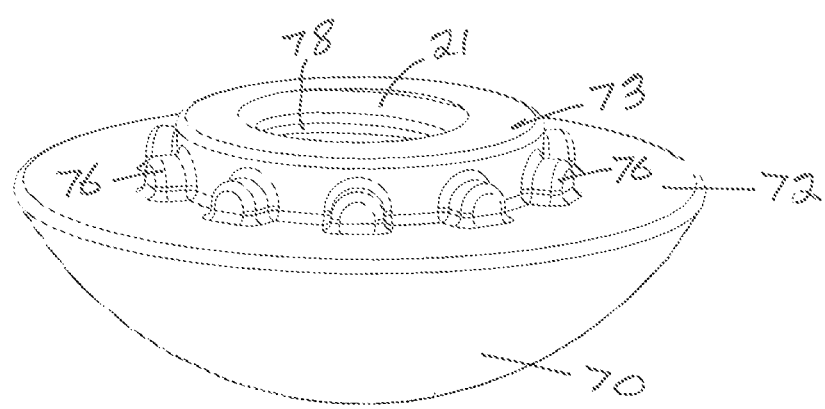
FIG. 7 is a perspective view of the distal end cap from another angle.
Figure 8:
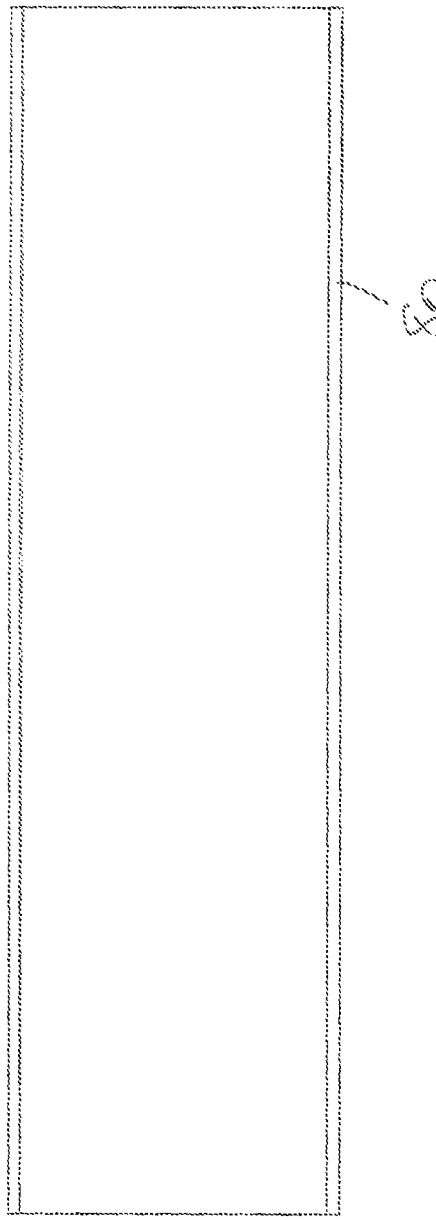
FIG. 8 is a perspective view of a resilient membrane of the prosthesis.
Figure 9:
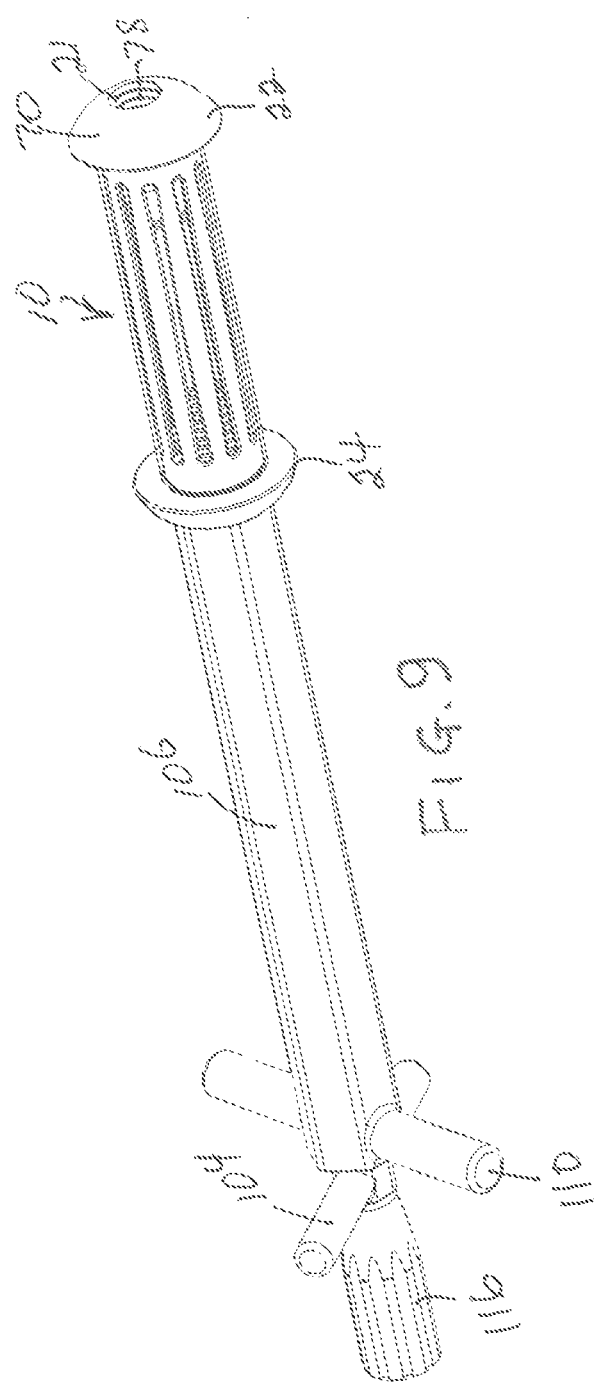
FIG. 9 is a perspective view of the prosthesis with implanting tools coupled.
Figure 10:
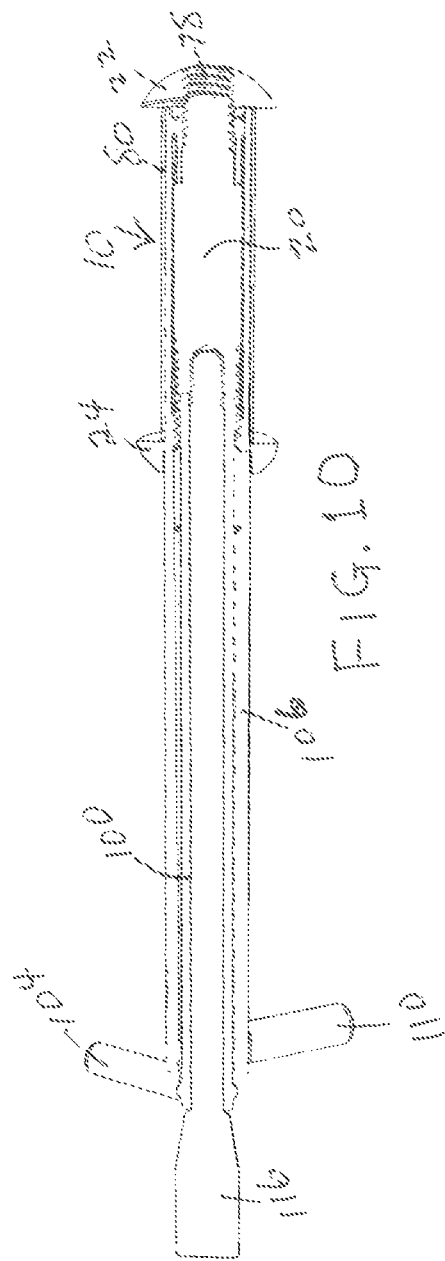
FIG. 10 is a sectional view taken through the mid-plane of the prosthesis of FIG. 9.

The implant tools are detachably coupled to the prosthesis as shown in FIGS. 9 and 10. The hex end 108 of the implant tool 92 is inserted into the hex opening 56 of the flanged proximal end cap 24. The hex end 102 of the implant tool 90 is inserted through the hollow hex tool 92 and inserted into the hex opening 41 of the rod 20. The threaded end 114 of the lead screw tool 94 is inserted through the hollow hex tool 90 and threaded into the threaded recess 45 of rod 20. The tools are now coupled to the prosthesis as shown in FIGS. 9 and 10. The prosthesis is now ready to be implanted into the spinal disc space. After implant, as will be described hereinafter, the prosthesis is expanded by relatively rotating the two hex tools 90 and 92. The threading is selected such that relative rotation in one sense results in the two end caps moving toward each other causing the bands 54 to bend or bow outwardly until they reach the condition as depicted in FIGS. 14 and 15, which is lower than the elastic limit of the bands 54. At this point the adjacent vertebrae have been moved apart to a vertical height greater than the height of normal disc space of the damaged intervertebral disc into which it is implanted. If it is desired to remove the prosthesis, then the prosthesis is contracted by relatively rotating the two hex tools 90 and 92 in the opposite directions from that which was used to expand the prosthesis. The selection of the threading is such that relative rotation in an opposite sense results in the two end caps moving apart from each other relieving the stress on the bands and letting the bands return inwardly until they reach their repose or at rest condition as depicted in FIG. 1. Continued relative rotation will case the distal end cap to become completely unscrewed from the rod 20 and fall off the prosthesis leaving the distal cap in the body.

Figure 16:
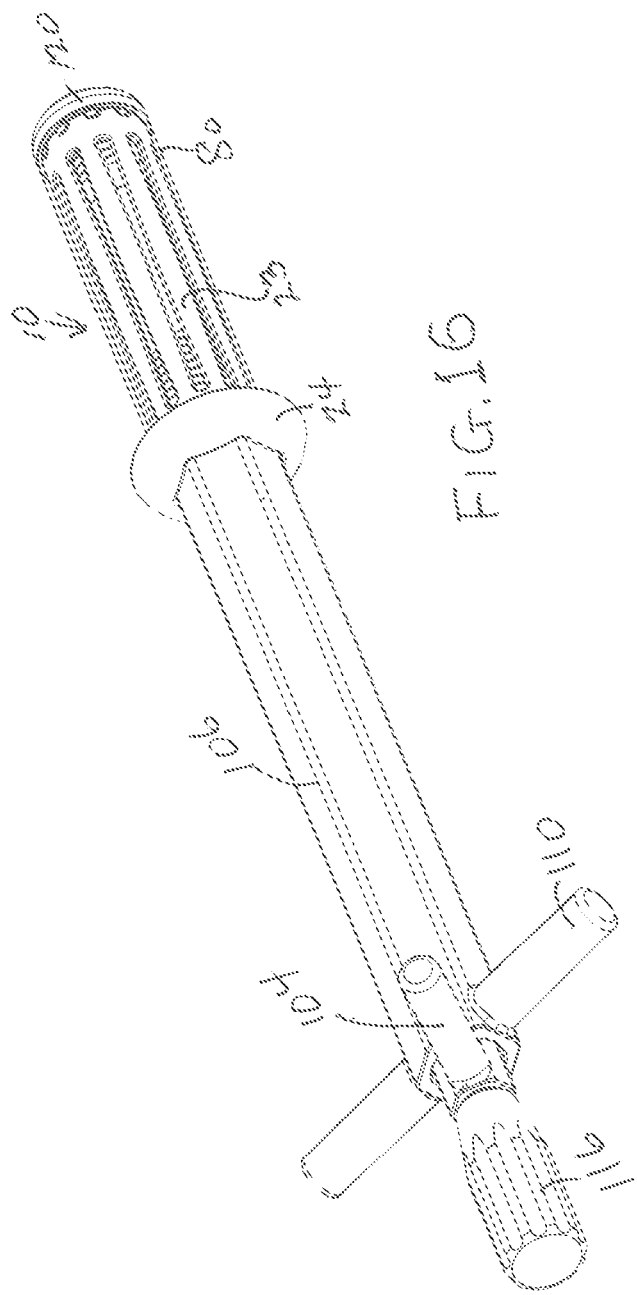
FIG. 16 is another embodiment of the prosthesis having a distal end cap without a flange with tools coupled.
Figure 17:
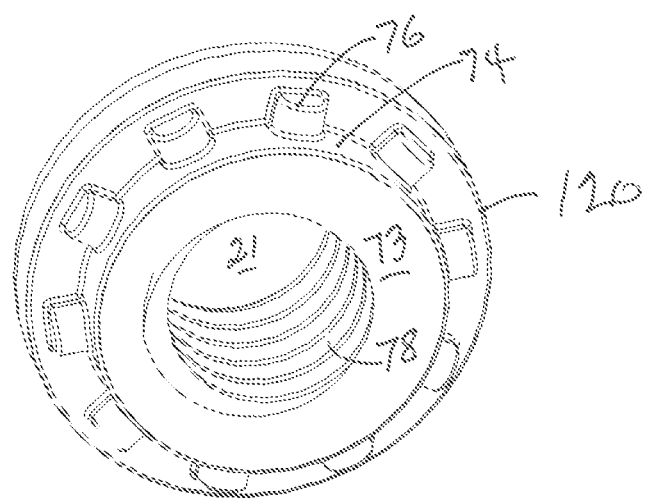
FIG. 17 is a perspective view of the distal end cap without a flange.

An alternative embodiment of prosthesis 10 is shown in FIGS. 16 and 17. As shown, the flanged end cap 22 has been replaced by a non-flanged end cap 120. No other change has been made. The structure of end cap 120 is the same as end cap 22 except there is no longer a flange. Therefore, during extraction of the prosthesis the entire prosthesis is removed.

Figure 18:
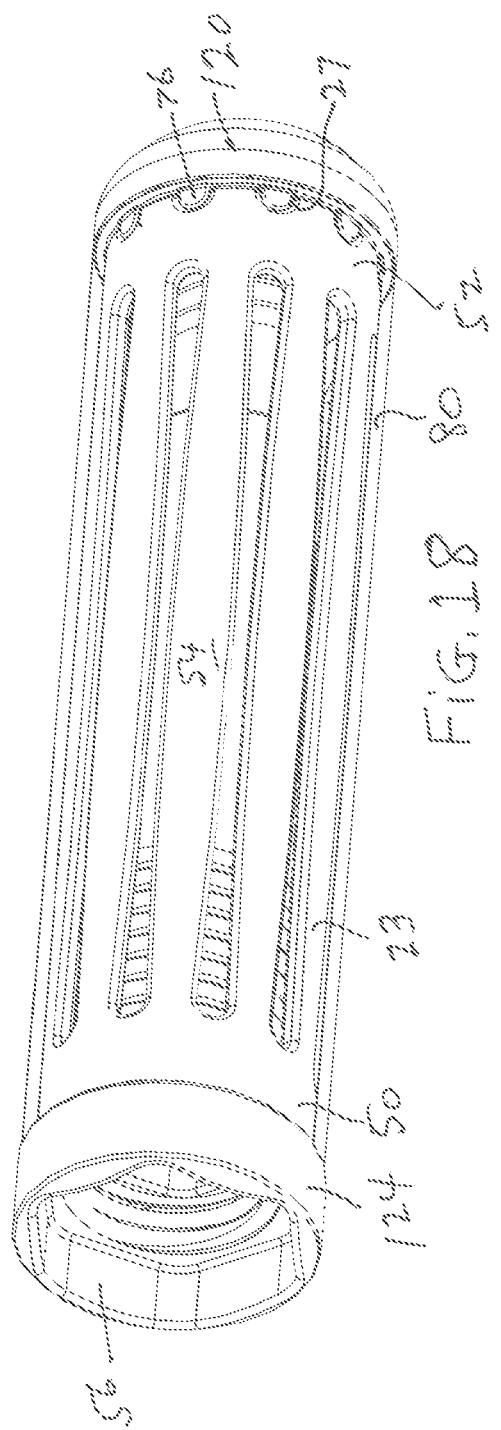
FIG. 18 is a perspective view of still another embodiment of the prosthesis using proximal and distal end caps without flanges.
Figure 19:
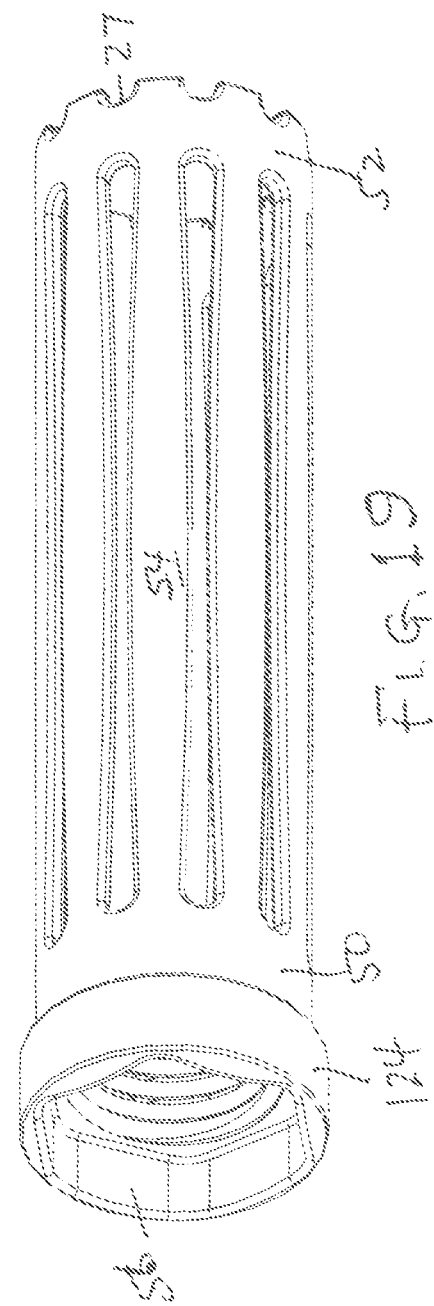
FIG. 19 is a perspective view of the main body portion of the prosthesis using proximal and distal end caps without flanges.

A still further embodiment of the prosthesis is shown in FIGS. 18 to 20. As shown, the flanges of both end caps 22 and 24 have been removed. The proximal end cap 24 is replaced by simple end cap 124, which has the same essential structure but without any flange. Therefore, the prosthesis can be implanted fully into the disc space and the entire prosthesis can be extracted.

The method for implanting and extracting the prosthesis will now be described in greater detail. In general, the following describes implanting: Insert hollow hex tool 92 in the large hex opening of the proximal cap 24 of the prosthesis. The hollow hex tool 90 is inserted into the hex opening of the lead screw 20. Note the lead screw tool 94 is threaded into the lead screw 20 simply for added stability while implanting, but it is also used for explanting. Turning the hex tool 92 in one direction or sense while turning the hex tool 90 in an opposite direction or sense compresses the prosthesis and expands it.

Note the distal end cap 22 will spin with the main body due to the engagement bumps 76 which key into the cutouts at the distal end of the tube 25 of the main body of the prosthesis.

To Explant: Again insert the three tools. Turning the hex tools 92 and 90 in the opposite directions or senses will allow the prosthesis to collapse and continued turning will eventually separate the prosthesis from the distal end cap 22. The prosthesis can now be pulled out, leaving the distal cap in the body.

The following are specific instructions for Implant and Explant for Expansible Prosthesis Versions as described herein.

A. Prosthesis with proximal and distal end caps.
  To Implant:
  1. Length and diameter of implant is chosen pre-operatively based on measurements from diagnostic imaging.
  2. A tube retractor or similar device goes in place against lateral aspect of spinal disc.
  3. Annulotomy drilled through disc under biplanar fluoroscopic guidance.
  4. Far end punctured with awl.
  5. Track is dilated under fluoroscopy with increasing-size dilators until desired size is reached. This confirms length and diameter of implant.
  6. Prosthesis is assembled and loaded onto the insertion tools (FIG. 9).
     a. Insert hollow hex tool 92 in the large hex opening of the proximal cap of the prosthesis 10.
     b. Hollow hex tool 90 is inserted into the hex opening of the lead screw 20.
     c. Note the lead screw tool 94 is threaded into the lead screw 20 simply for added stability while implanting, but it is also used for explanting.
  7. Whole assembly is placed through the tube retractor against the side of the spinal disc at the annulotomy hole.
  8. Mallet is used to tap prosthesis through-and-through the disc under fluoroscopic guidance.
  9. Proximal head 24 stops prosthesis when fully inserted; distal end cap 22 projects somewhat beyond distal disc annulus.
  10. Hex tool 90 is turned in one direction or sense while turning the hex tool 92 is turned in the opposite direction or sense so end caps move toward each other.
     a. This compresses the prosthesis and expands it.
     b. Note the distal end cap 22 will not spin due to the engagement bumps 76 which key into the cutouts 27 at the distal end of tube 25.
     c. Expansion of the prosthesis 10 pulls distal end cap 22 back to distal disc annulus.
  11. Implant tools are removed leaving expanded prosthesis in place.
  To Explant:
  1. Tube retractor goes in place against lateral aspect of disc.
  2. Again insert the three tools.
  3. Turn hex tool 90 in appropriate direction or sense while turning hex tool 92 in the opposite direction or sense so end caps move apart.
     a. Prosthesis collapses and separates from distal end cap.
  4. Pull assembly out, leaving the distal cap in body.
  B. Prosthesis with only proximal flanged end cap and distal end cap being without flange.
  To Implant:
  1. Length and diameter of implant is chosen pre-operatively based on measurements from diagnostic imaging.
  2. Tube retractor goes in place against lateral aspect of disc.
  3. Annulotomy is made in side of disc under biplanar fluoroscopic guidance without creating an annulotomy at distal side of disc.
  4. Annulotomy opening is dilated with increasing-size dilators until desired size is reached.
  5. Prosthesis is assembled and loaded onto the insertion tools (FIG. 16).
     a. Insert hollow hex tool 92 in the large hex opening of the proximal cap 24 of the prosthesis 10.
     b. Hollow hex tool 90 is inserted into the hex opening of the lead screw 20.
     c. Note the lead screw tool 94 is threaded into the lead screw 20 simply for added stability while implanting, but it is also used for explanting.
  6. Whole assembly is placed through the tube retractor against the side of the disc at the annulotomy hole.
  7. Mallet is used to tap prosthesis into the disc under fluoroscopic guidance.
  8. Proximal head 24 stops prosthesis when fully inserted.
  9. Hex tool 90 is turned in one direction or sense while turning the hex tool 92 in an opposite direction or sense to move the end caps 22 and 24 toward each other.
     a. This compresses the prosthesis and expands it inside the disc.
  10. Implant tools are removed leaving expanded prosthesis in place.
  To Explant:
  1. Tube retractor goes in place against lateral aspect of disc.
  2. Again insert the three tools.
  3. Turn hex tool 90 in a direction and sense while turning hex tool 92 in an opposite direction or sense to move end caps apart.
     a. Prosthesis collapses.
  4. Pull assembly out.
  C. Prosthesis with no flanged end caps.
  To Implant:
  1. Length and diameter of implant is chosen pre-operatively based on measurements from diagnostic imaging.
  2. Tube retractor goes in place against lateral aspect of spinal disc.
  3. Annulotomy is made in side of disc under biplanar fluoroscopic guidance without creating an annulotomy at distal side of disc.
  4. Annulotomy opening is dilated with increasing-size dilators until desired size is reached.
  5. Prosthesis (FIG. 18) is assembled and loaded onto the insertion tools.
  6. Assembly is placed through the tube retractor against the side of the disc at the annulotomy hole.
  7. Mallet is used to tap prosthesis into the disc under fluoroscopic guidance.
  8. Tools are turned in opposite directions, compressing and expanding the prosthesis inside the disc.
  9. Implant tools are removed leaving expanded prosthesis in place.
  To Explant:
  1. Tube retractor goes in place against lateral aspect of disc.
  2. Again insert the three tools.
  3. Turn tools in opposite directions, collapsing the prosthesis inside the disc.
  4. Pull assembly out.

Although the invention has been described in specific embodiments, changes and modifications will be evident to persons skilled in the art, which do not depart from the spirit and scope of the teachings herein. Such changes are deemed to fall within the purview of the invention as claimed.

What is claimed is:

1. An expandable spinal prosthesis having a proximal end and a distal end for insertion unilaterally into a through annulotomy hole created laterally in a spinal disc at its mid-plane between two abutting vertebrae, the prosthesis comprising an elongated rod having first threading at its proximal end and second threading at its distal end, a first member comprised of a proximal end cap and a hollow tube fixed thereto extending distally threaded on the threading at the proximal end of said rod, a second member comprised of a distal end cap threaded on the threading at the distal end of said rod, the distal end of the hollow tube being non-threadingly disengageably engaged with the distal end cap, whereby said first and second members are disengageably engaged for rotation together, said proximal end cap and said distal end cap being preselected to having a diameter greater than the diameter of the through annulotomy hole so that when the prosthesis is in place in the through annulotomy hole the proximal end cap and said distal end cap are outside the annulotomy hole and can engage the two abutting vertebrae, the hollow tube of said first member having a plurality of resiliently deformable bands extending longitudinally between the proximal end cap and the distal end cap, said bands having a preselected elastic limit and in repose lie flat between said first proximal end cap and said second distal end cap, the first member and the elongated rod defining engagements for coupling of drivers to rotate the first and second members relative to the rod in one sense so that the first and second members will move toward each other to cause the resiliently deformable bands to bend outwardly without exceeding the preselected elastic limit of the bands to expand the prosthesis to a diameter greater than the distance separating the two abutting vertebrae and enable said proximal end cap and said distal end cap to engage the two abutting vertebrae to hold the prosthesis in position and in an opposite sense so that the first and second members will move apart to cause the resilient bands to become unbent and collapse the prosthesis and to enable the second distal cap to become unthreaded from the elongated rod, whereby the prosthesis can be removed unilaterally from the annulotomy hole, wherein one of the distal end cap and the hollow tube has at least one engagement bump and the other of the distal end cap and the hollow tube has at least one cutout, the at least one engagement bump mates with the at least one cutout preventing rotation of the distal end cap relative to the hollow tube.

2. The expandable spinal prosthesis according to claim 1 wherein the engagements defined by the first member and rod are recesses.

3. The expandable spinal prosthesis according to claim 2 wherein the recesses are non-circular shaped.

4. The expandable spinal prosthesis according to claim 3 wherein the recesses are hex shaped.

5. The expandable spinal prosthesis according to claim 1 wherein a resilient membrane covers the prosthesis.

6. The expandable spinal prosthesis according to claim 1 wherein the proximal end of the elongated rod has a greater diameter than the distal end of the elongated rod.

7. The expandable spinal prosthesis according to claim 6 wherein the distal end of said tube has a plurality of cutouts and the distal end cap has a plurality of engagement bumps.

8. The expandable spinal prosthesis according to claim 6 wherein the proximal and distal end caps are flanged to enable engagement with the abutting vertebrae to the spinal disc undergoing treatment when the prosthesis is placed unilaterally in the spinal disc to hold the prosthesis in position.

9. A method of inserting an expandable spinal prosthesis according to claim 1 comprising the steps of: a) creating a through annulotomy hole laterally in the mid-plane of a spinal disc between two abutting vertebrae, said annulotomy hole having a proximal end and a distal end; b) unilaterally inserting the prosthesis, having a repose length greater than the length of the annulotomy hole, in the proximal end of the annulotomy hole and pushing through so that the distal end of the prosthesis projects out of the distal end of the annulotomy hole;

c) relatively rotating the first member and the elongated rod to cause the proximal end cap and the distal end cap to move toward each other to cause the prosthesis to expand outwardly; d) wherein the prosthesis causes the abutting vertebrae to intentionally distract to the desired degree and for the desired purpose; and e) wherein the proximal end cap and the distal end cap engage the abutting vertebrae to hold the prosthesis in position.

10. The method according to claim 9 further including the steps of explanting the prosthesis by a. accessing the prosthesis unilaterally; b. relatively rotating the first member and the elongated rod to cause the proximal end cap and the distal end cap to move apart to cause the bands of the prosthesis to collapse inwardly and to cause the distal end cap to fall off the elongated rod; and c. withdrawing the prosthesis from the annulotomy hole.

* * * * *